(12) United States Patent
Miyazawa et al.

(10) Patent No.: US 11,537,916 B2
(45) Date of Patent: Dec. 27, 2022

(54) OPTIMIZATION APPARATUS, CONTROL METHOD FOR OPTIMIZATION APPARATUS, AND RECORDING MEDIUM

(71) Applicant: FUJITSU LIMITED, Kawasaki (JP)

(72) Inventors: Toshiyuki Miyazawa, Kawasaki (JP); Takayuki Shibasaki, Kawasaki (JP); Taiki Uemura, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 296 days.

(21) Appl. No.: 16/898,484

(22) Filed: Jun. 11, 2020

(65) Prior Publication Data
US 2020/0410372 A1 Dec. 31, 2020

(30) Foreign Application Priority Data
Jun. 27, 2019 (JP) .............................. JP2019-119604

(51) Int. Cl.
*G06F 15/16* (2006.01)
*G06N 5/04* (2006.01)
(Continued)

(52) U.S. Cl.
CPC ............... *G06N 5/04* (2013.01); *G06N 20/00* (2019.01); *G16B 15/00* (2019.02)

(58) Field of Classification Search
CPC ........... G06N 5/04; G06N 20/00; G16B 15/00
(Continued)

(56) References Cited

U.S. PATENT DOCUMENTS 7,319,943 B2 * 1/2008 Washizawa ............. G06F 17/11
703/2
7,433,743 B2 * 10/2008 Pistikopoulos ........ G05B 17/02
700/89
(Continued)

FOREIGN PATENT DOCUMENTS

| JP | 2015-191340 A | 11/2015 |
|---|---|---|
| JP | 2016-051350 A | 4/2016 |

OTHER PUBLICATIONS

Gili Rosenberg and et al., "Building an Iterative Heuristic Solver for a Quantum Annealer", Computational Optimization and Applications, 65, 3, 845, 2016, arXiv:1507.07605v2 [cs.DM] (Total 21 pages).

(Continued)

*Primary Examiner* — Moustafa M Meky
(74) *Attorney, Agent, or Firm* — Fujitsu Patent Center

(57) ABSTRACT

An optimization apparatus includes a memory; and a processor coupled to the memory and the processor configured to: compute a local solution for a combinatorial optimization problem based on a first evaluation function representing the combinatorial optimization problem, select a state variable group targeted by partial problems from the plurality of state variables based on a first state variable whose value at the local solution is a predetermined value among the plurality of state variables included in the first evaluation function, a weight coefficient representing a magnitude of an interaction between the plurality of state variables held in a storage unit, and input selection region information, search a ground state for a second evaluation function representing the partial problems for the selected state variable group, and generate a whole solution by updating the local solution based on the partial solutions acquired by the ground state search.

9 Claims, 16 Drawing Sheets

(51) Int. Cl.
  *G06N 20/00* (2019.01)
  *G16B 15/00* (2019.01)
(58) Field of Classification Search
  USPC .......................................................... 709/200
  See application file for complete search history.

(56) References Cited

U.S. PATENT DOCUMENTS

| | | | | |
|---|---|---|---|---|
| 7,676,350 | B2* | 3/2010 | Washizawa | G06F 17/11 700/47 |
| 9,702,997 | B2* | 7/2017 | Sava | G01V 1/303 |
| 2002/0143798 | A1* | 10/2002 | Lisiecki | H04L 67/1097 |
| 2004/0143798 | A1* | 7/2004 | Washizawa | G06F 17/11 703/2 |
| 2005/0107895 | A1* | 5/2005 | Pistikopoulos | G05B 13/048 700/74 |
| 2008/0015828 | A1* | 1/2008 | Washizawa | G06F 17/11 703/2 |
| 2015/0278408 | A1 | 10/2015 | Yoshimura et al. | |
| 2016/0063391 | A1 | 3/2016 | Hayashi et al. | |

OTHER PUBLICATIONS

Babej, Tomas et al., "Coarse-grained lattice protein folding on a quantum annealer", arxiv.org, Cornell University Library, 201 Olin Library Cornell University Ithaca, NY 14853, Nov. 2, 2018, XP080941413, pp. 1-12.

Perdomo-Ortiz, Alejandro et al., "Finding low-energy conformations of lattice protein models by quantum annealing", Scientific Reports, vol. 2, No. 1, Aug. 13, 2012, XP055676849, pp. 1-7.

Aramon, Maliheh et al., "Physics-Inspired Optimization for Quadratic Unconstrained Problems Using a Digital Annealer", arxiv.org, Cornell University Library, 201 Olin Library Cornell University Ithaca, NY 14853, Apr. 7, 2018, XP081200633.

Shaydulin, Ruslan et al., "Network Community Detection on Small Quantum Computers", arxiv.org, Cornell University Library, 201 Olin Library Cornell University Ithaca, NY 14853, Feb. 22, 2019, XP081020455, pp. 1-13.

Extended European Search Report dated Dec. 21, 2020 for corresponding European Patent Application No. 20178405.5, 10 pages.

* cited by examiner

FIG. 14

| CONDITION | PROBLEM BIT SIZE | OPTIMIZATION CALCULATION BIT SIZE | NUMBER OF HARDWARE CALLS | NUMBER OF ITERATIONS FOR ONE CALL | PERCENTAGE OF CORRECT ANSWERS | TOTAL NUMBER OF ITERATIONS | ITS | ITS × OPTIMIZATION CALCULATION BIT SIZE |
|---|---|---|---|---|---|---|---|---|
| DIVIDED (Hardware) | 3.10E+04 | 8.00E+03 | 5 | 2.00E+07 | 0.99 | 1.00E+08 | 1.00E+08 | 8.00E+11 |
| NON-DIVIDED (Simulation) | 3.10E+04 | 3.10E+04 | 1 | 7.42E+06 | 0.99 | 7.42E+06 | 7.42E+06 | 2.30E+11 |
| DIVIDED (Hardware) | 7.80E+03 | 1.00E+03 | 6 | 1.00E+06 | 0.86 | 6.00E+06 | 1.41E+07 | 1.41E+10 |
| NON-DIVIDED (Simulation) | 7.80E+03 | 7.80E+03 | 1 | 2.33E+06 | 0.99 | 2.33E+06 | 2.33E+06 | 1.82E+10 |

OPTIMIZATION APPARATUS, CONTROL METHOD FOR OPTIMIZATION APPARATUS, AND RECORDING MEDIUM

CROSS-REFERENCE TO RELATED APPLICATION

This application is based upon and claims the benefit of priority of the prior Japanese Patent Application No. 2019-119604, filed on Jun. 27, 2019, the entire contents of which are incorporated herein by reference.

FIELD

The embodiments discussed herein are related to an optimization apparatus, a control method for the optimization apparatus, and a recording medium.

BACKGROUND

Combinatorial optimization problems exist in various fields in the present society. For example, a combination of elements for optimizing (minimizing) the cost is searched in a field such as manufacturing, physical distribution and marketing fields. However, in a combinatorial optimization problem, as the number of variables corresponding to the elements above increases, the calculation time exponentially increases. Therefore, a problem has been known that it is difficult to solve a combinatorial optimization problem by using a von Neumann computer in the past.

As a method for solving a combinatorial optimization problem with many variables that is difficult for such a von Neumann computer to handle, the combinatorial optimization problem to be calculated is replaced by an Ising model that is a model representing a behavior of spins of a magnetic substance for calculation. By performing simulated annealing by using a digital circuit as hardware that solves a combinatorial optimization problem by applying the Ising model, a combination of values of state variables resulting in a minimum value of an Ising type evaluation function may be calculated. The similar calculation may be performed by performing quantum annealing by using a superconducting circuit.

On the other hand, because of constraints such as a hardware amount and a memory size for calculation by software, there is a method that divides a combinatorial optimization problem having a large problem size (or higher number of state variables (corresponding to the number of spins of an Ising model)) into small problems for calculation. For example, there is a method that generates partial problems acquired by dividing a combinatorial optimization problem to be calculated, searches solutions for the partial problems and generates a solution of the whole problem based on the solutions for the partial problems (see Japanese Laid-open Patent Publication No. 2016-51350, Japanese Laid-open Patent Publication No. 2015-191340, and Rosenberg, and et. al., "Building an Iterative heuristicsolver for a quantum annealer", Computational Optimization and Applications, 65, 3, 845, 2016, for example).

SUMMARY

According to an aspect of the embodiments, an optimization apparatus includes a memory; and a processor coupled to the memory and the processor configured to: compute a local solution for a combinatorial optimization problem based on a first evaluation function representing the combinatorial optimization problem, select a state variable group targeted by partial problems from the plurality of state variables based on a first state variable whose value at the local solution is a predetermined value among the plurality of state variables included in the first evaluation function, a weight coefficient representing a magnitude of an interaction between the plurality of state variables held in a storage unit, and input selection region information, search a ground state for a second evaluation function representing the partial problems for the selected state variable group, and generate a whole solution by updating the local solution based on the partial solutions acquired by the ground state search.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 14 is a diagram illustrating a comparison example of amounts of complexity based on the presence of division of a problem;

DESCRIPTION OF EMBODIMENTS

In a case where a combinatorial optimization problem to be calculated is divided for calculation, because of an influence of calculation processing of acquiring a solution of the whole combinatorial optimization problem based on solutions of partial problems thereof, for example, the amount of complexity up to the acquisition of the solution of the whole problem disadvantageously increases more than a case where the solution of the whole problem is acquired without dividing the problem.

In one aspect, it is an object of the embodiments to provide an optimization apparatus, a control method for the optimization apparatus, and a recording medium, which may suppress an increase of the amount of complexity when a combinatorial optimization problem is divided for calculation.

Embodiments of the present disclosure will be described below with reference to the drawings.

First Embodiment

Figure 1:
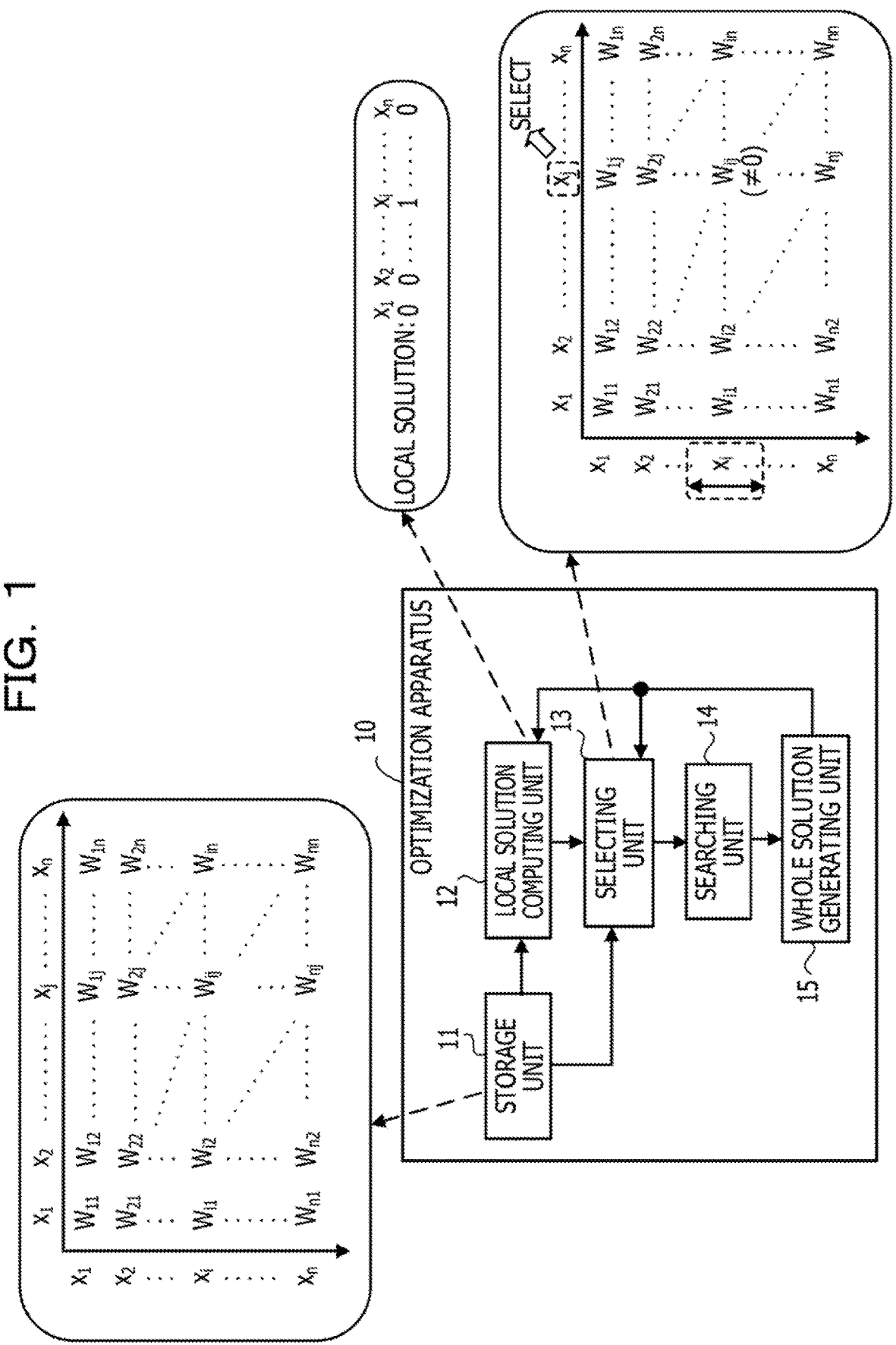
FIG. 1 is a diagram illustrating an example of an optimization apparatus according to a first embodiment.

FIG. 1 is a diagram illustrating an example of an optimization apparatus according to a first embodiment.

An optimization apparatus 10 according to the first embodiment includes a storage unit 11, a local solution computing unit 12, a selecting unit 13, a searching unit 14, and a whole solution generating unit 15.

The storage unit 11 holds weight coefficients representing the magnitudes of interactions between a plurality of state variables included in an evaluation function representing a combinatorial optimization problem. The storage unit 11 is a volatile storage device such as a random-access memory (RAM) or a non-volatile storage device such as a hard disk drive (HDD) or a flash memory, for example.

Combinatorial optimization problems to be calculated include, for example, a problem for searching a stable structure of a straight-chain structure with a plurality of amino adds (amino add residues) and a traveling salesman problem. When these problems are considered as more practical problems, it is known that the number of state variables therein is significantly high. Because of constraints of the hardware amount and a memory size for calculation by software, the problems are preferably divided into partial problems for calculation. However, the problems to be calculated are not limited to the problems described above.

An Ising type evaluation function (also called an "energy function") E(x) using a weight coefficient is defined by the following expression (1), for example.

$$E(x) = -\sum_{\langle i,j \rangle} W_{ij} x_i x_j - \sum_i b_i x_i \qquad (1)$$

The first term on the right side adds up the products of two state variable values (0 or 1) and a weight coefficient without missing and overlapping among all combinations of two state variables selectable from all state variables included in the evaluation function. $x_i$ is a state variable with an identification number of i, $x_j$ is a state variable representing a value of a bit with an identification number of j, and $W_{ij}$ is a weight coefficient representing the magnitude of an interaction between $x_i$ and $x_j$. In this case, $W_{ii}=0$. The relationship $W_{ij}=W_{ji}$ p is often satisfied (or the coefficient matrix with the weight coefficient is often a symmetric matrix).

For example, as illustrated in FIG. 1, when the total number of state variables is equal to n, the storage unit 11 holds n×n weight coefficients. The values of the weight coefficients reflect characteristics of a combinatorial optimization problem to be calculated.

The n×n weight coefficients may be obtained externally to the optimization apparatus 10, or the optimization apparatus 10 may compute them based on input problem data.

The local solution computing unit 12 computes local solutions for a combinatorial optimization problem based on the evaluation function as expressed in Expression (1). The local solution computing unit 12 computes local solutions by tabu search, for example. Because the local solutions are used as initial solutions for search processing by the searching unit 14, which will be described below, the local solutions may not be an optimum solution. The local solution computing unit 12 may compute local solutions by handling a whole solution generated by the whole solution generating unit 15, which will be described below, as an initial solution.

The selecting unit 13 selects a state variable group targeted by partial problems from a plurality of state variables based on state variables whose values at local solutions are a predetermined value among a plurality of state variables, weight coefficients, and input selection region information.

For example, in Expression (1), when a state variable having a value of 1 is a first state variable and a state variable that interacts with the first state variable is a second state variable, there is a possibility that the value of the evaluation function changes in accordance with the value of the second state variable. In other words, for example, there is a possibility that the value of the second state variable is updated such that the value of the evaluation function decreases (more closely to a ground state). Accordingly, the selecting unit 13 selects the second state variable as a candidate to be included in the state variable group based on the weight coefficient.

However, there is possibility that the value of the weight coefficient is significantly high if the value of the weight coefficient expresses a constraint term of the evaluation function, which will be described below. The selecting unit 13 does not include the second state variable with the magnitude of interaction with the first state variable expressed by such a weight coefficient in the state variable group because there is a possibility that, if the value of the second state variable is 1, the constraint condition represented by the constraint term is not satisfied. In order to implement this functionality, a range of the values of the weight coefficients used for selecting the state variable group is included in the input selection region information.

In order to increase the number of state variables to be included in the state variable group, the selecting unit 13 may perform processing of selecting a second state variable to be included in the state variable group also based on the weight coefficient on a predetermined number of state variables having identification numbers dose to that of the first state variable, for example. The predetermined number is also included in the selection region information, for example. The predetermined number is determined in accordance with the number of computing bits processable by the searching unit 14, for example. The number of computing bits may also be included in the selection region information. For higher efficiency of the processing by the searching unit 14, an equal number of state variables to the number of computing bits processable by the searching unit 14 are desirably included in the state variable group.

The selecting unit 13 may update the state variable group to be selected based on state variables having predetermined values as values in the whole solution generated by the whole solution generating unit 15, which will be described below, the weight coefficients, and the selection region information.

The searching unit 14 searches a ground state for the evaluation function representing the partial problems for the state variable group selected by the selecting unit 13. The searching unit 14 may perform the search for a ground state by simulated annealing or Markov chain Monte Carlo methods such as a replica exchange method or may perform the search for a ground state by quantum annealing. The evaluation function representing partial problems is acquired by changing the state variables included in Expression (1) to the selected state variable group.

The states being solutions (partial solutions) for partial problems acquired by the ground state search (values of the selected state variable group) are states minimizing the value of the evaluation function representing the partial problems among states updated a predetermined number of times, for example.

The whole solution generating unit 15 generates a whole solution by updating local solutions based on partial solutions. For example, the whole solution generating unit 15 generates a whole solution by replacing values of the selected state variable group indicated by partial solutions by values of corresponding state variable group in the local solutions.

The local solution computing unit 12, the selecting unit 13, the searching unit 14, and the whole solution generating unit 15 may be implemented by using program modules executed by a processor such as a central processing unit (CPU) or a digital signal processor (DSP). The searching unit 14 may be hardware that executes simulated annealing or a replica exchange method by using a digital circuit or may be hardware that performs quantum annealing.

An example of operations of the optimization apparatus 10 (control method for the optimization apparatus 10) according to the first embodiment will be described below.

Figure 2:
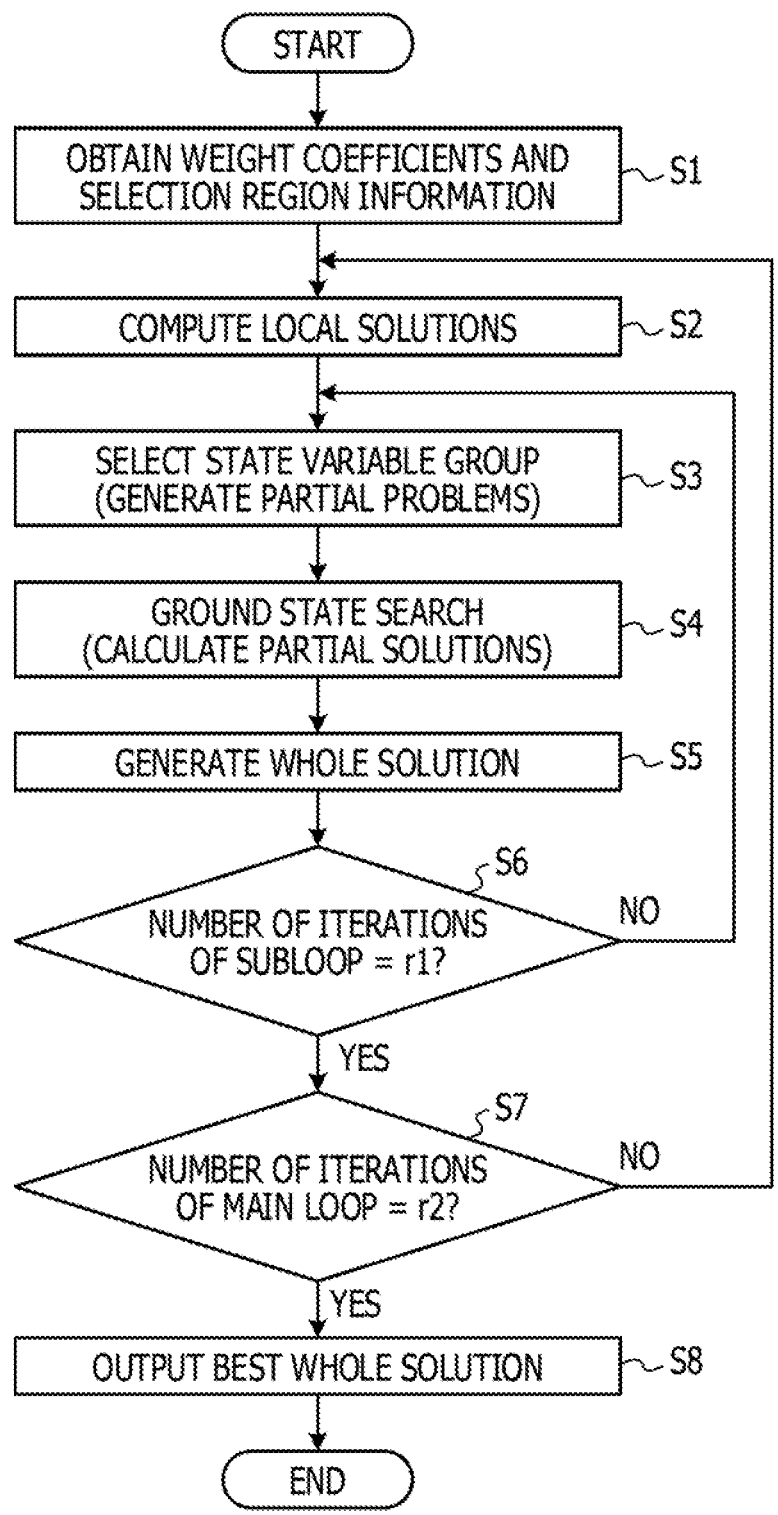
FIG. 2 is a flowchart illustrating a flow of an example of a control method for the optimization apparatus according to the first embodiment.

FIG. 2 is a flowchart illustrating a flow of an example of a control method for the optimization apparatus according to the first embodiment.

An input unit, not illustrated, in the optimization apparatus 10 obtains weight coefficients and selection region information as described above (step S1). The weight coefficients are stored in the storage unit 11 (the selection region information may also be stored in the storage unit 11). The local solution computing unit 12 computes local solutions for a combinatorial optimization problem based on the evaluation function as expressed in Expression (1), for example (step S2). FIG. 1 illustrates an example of local solutions. In the example in FIG. 1, $x_i$ has a value of 1 among n state variables ($x_i$ to $x_n$).

The selecting unit 13 selects a state variable group targeted by partial problems from a plurality of state variables based on a state variable whose value at local solutions is a predetermined value among a plurality of state variables, a weight coefficient, and input selection region information (step S3). FIG. 1 illustrates an example in which a state variable group is selected based on a state variable having a value of 1 (the first state variable described above), weight coefficients, and input selection region information. For example, when x has a value of 1 and $W_{ij}$ does not have a value of 0 (that is a value within a predetermined range indicated in the selection region information), $x_j$ is selected as one of the state variable group by priority. The selecting unit 13 performs the processing of selecting state variables to be included in the state variable group also based on the weight coefficients on a predetermined number of state variables having identification numbers close to that of $x_i$.

After that, the searching unit 14 calculates partial solutions by searching a ground state for the evaluation function representing partial problems for the state variable group selected by the selecting unit 13 (step S4). The whole solution generating unit 15 generates a whole solution by updating the local solutions based on the partial solutions (step S5).

After that, for example, the whole solution generating unit 15 determines whether the number of iterations of the processing in steps S3 to S5 (the number of iterations of the subloop) is equal to a predetermined number (r1) or not (step S6). If it is determined that the number of iterations of the subloop=r1 is not satisfied, the processing from step S3 is repeated. In the second and subsequent processing of the subloop, the selecting unit 13 updates the state variable group targeted by the partial problems based on the whole solution generated by the whole solution generating unit 15.

If it is determined that the number of iterations of the subloop=1 is satisfied, the whole solution generating unit 15 determines whether the number of iterations of the processing in steps S2 to S6 (the number of iterations of the main loop) is equal to a predetermined number (r2) or not (step S7). If it is determined that the number of iterations of the main loop=r2 is not satisfied, the processing from step S2 is repeated. In the second and subsequent processing of the main loop, the local solution computing unit 12 computes local solutions by handling the whole solution generated by the whole solution generating unit 15 as an initial solution.

If it is determined that the number of iterations of the main loop=r2 is satisfied, the whole solution generating unit 15 outputs a whole solution minimizing the value of the evaluation function among whole solutions acquired up to this point as the best whole solution, for example (step S8).

The order of the operations of the processing is not limited to the example in FIG. 2 but may be interchanged properly.

In this manner, in a case where the optimization apparatus 10 divides a combinatorial optimization problem into partial problems, a state variable group targeted by the partial problems is selected based on state variables having values being a predetermined value in local solutions and weight coefficients so that the proper division may be achieved by reflecting a characteristic of the combinatorial optimization problem. As described above, in a case where a combinatorial optimization problem to be calculated is generally divided for calculation, the amount of complexity up to the acquisition of the solution of the whole problem increases more than the calculation without the division because of, for example, an influence of the calculation processing for acquiring a whole solution based on solutions for the partial problems. When the state variable group targeted by partial problems is randomly selected simply based on random numbers, it is difficult to reflect a characteristic of the combinatorial optimization problem to the partial problems. Because of this, when the calculation using such partial problems is performed, many iterative calculations are to be performed for acquiring a highly precise whole solution. There is a possibility that the amount of complexity increases more. On the other hand, because the optimization apparatus 10 may achieve proper division reflecting a characteristic of a combinatorial optimization problem as described above, the increase of the amount of complexity up to the acquisition of a highly precise whole solution may be suppressed.

Second Embodiment

Figure 3:
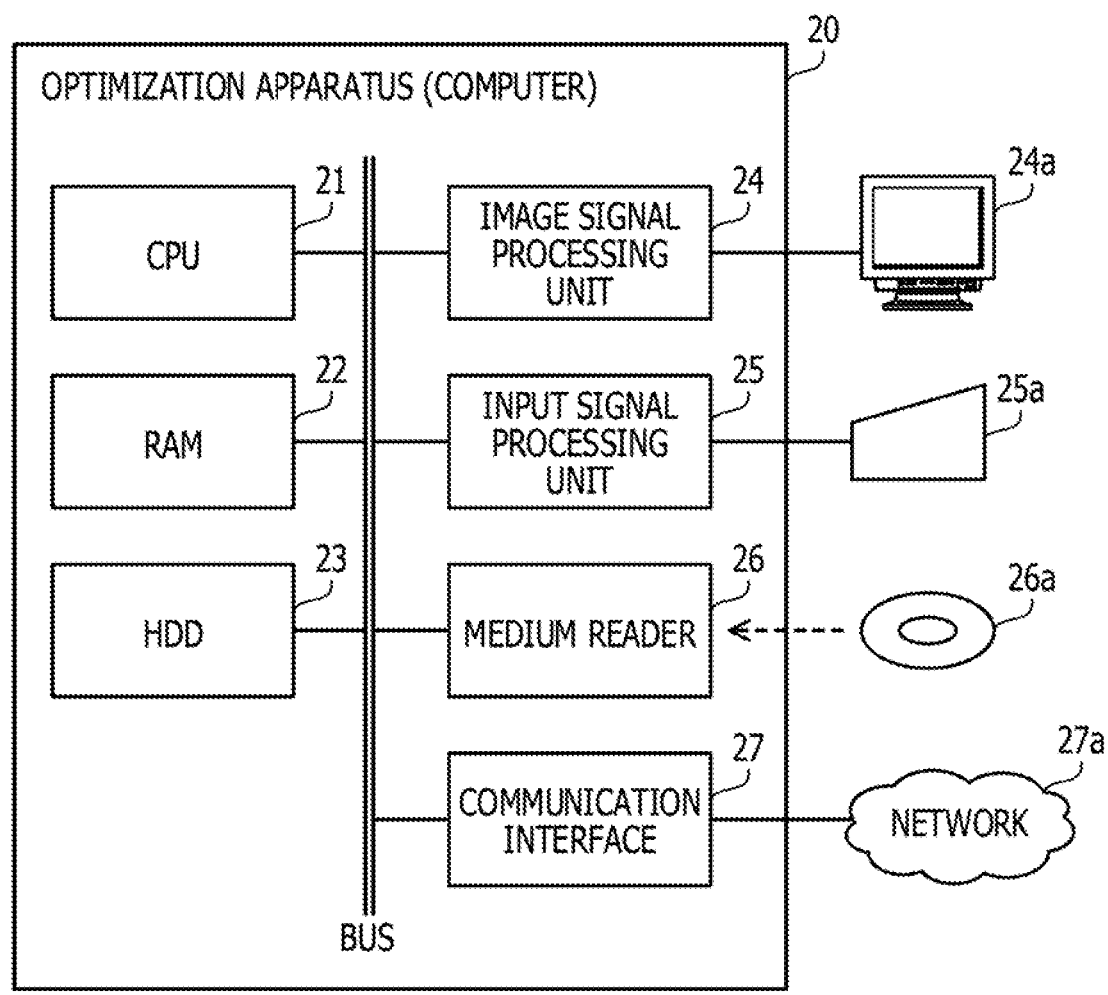
FIG. 3 is a diagram illustrating a hardware example of an optimization apparatus according to a second embodiment.

FIG. 3 is a diagram illustrating a hardware example of an optimization apparatus according to a second embodiment.

An optimization apparatus 20 according to the second embodiment is a computer, for example, and includes a CPU 21, a RAM 22, an HDD 23, an image signal processing unit 24, an input signal processing unit 25, a medium reader 26, and a communication interface 27. The above units are coupled to a bus.

The CPU 21 is a processor including an arithmetic circuit that executes program instructions. The CPU 21 loads at least a part of a program and data stored in the HDD 23 into the RAM 22 and executes the program. The CPU 21 may include a plurality of processor cores, the optimization apparatus 20 may include a plurality of processors, and the processes, which will be described below, may be executed in parallel using a plurality of processors or processor cores. A set of the plurality of processors (multiprocessor) may be referred to as a "processor".

The RAM 22 is a volatile semiconductor memory that temporarily stores a program executed by the CPU 21 and data used for computation by the CPU 21. The optimization apparatus 20 may include a type of memory other than the RAM, and may include a plurality of memories.

The HDD 23 is a non-volatile storage device that stores software programs such as an operating system (OS), middleware and application software, and data. The programs include a control program for the optimization apparatus 20, for example. The optimization apparatus 20 may include other types of storage devices such as a flash memory and a solid state drive (SSD), and may include a plurality of non-volatile storage devices.

The image signal processing unit 24 outputs an image to a display 24a coupled to the optimization apparatus 20 in accordance with an instruction from the CPU 21. The display 24a may be a cathode ray tube (CRT) display, a liquid crystal display (LCD), a plasma display panel (PDP), an organic electro-luminescence (OEL) display or the like.

The input signal processing unit 25 obtains an input signal from an input device 25a coupled to the optimization apparatus 20 and outputs the input signal to the CPU 21. As the input device 25a, a pointing device such as a mouse, a touch panel, or a trackball, a keyboard, a remote controller, a button switch and the like may be used. A plurality of types of input devices may be coupled to the optimization apparatus 20.

The medium reader 26 is a reading device that reads a program or data recorded on a recording medium 26a. As the recording medium 26a, for example, a magnetic disk, an optical disk, a magneto-optical disk (MO), a semiconductor memory and the like may be used. The magnetic disk includes a flexible disk (FD) and an HDD. The optical disk includes a compact disc (CD) and a digital versatile disc (DVD).

The medium reader 26 copies a program or data read from the recording medium 26a to another recording medium such as the RAM 22 or the HDD 23, for example. The read program is executed by the CPU 21, for example. The recording medium 26a may be a portable recording medium or may be used to distribute the program or data. The recording medium 26a and the HDD 23 may be referred to as computer-readable recording media.

The communication interface 27 is coupled to a network 27a and communicates with another information processing apparatus via the network 27a. The communication interface 27 may be a wired communication interface coupled to a communication device such as a switch via a cable, or may be a wireless communication interface coupled to a base station via a wireless link.

Figure 4:
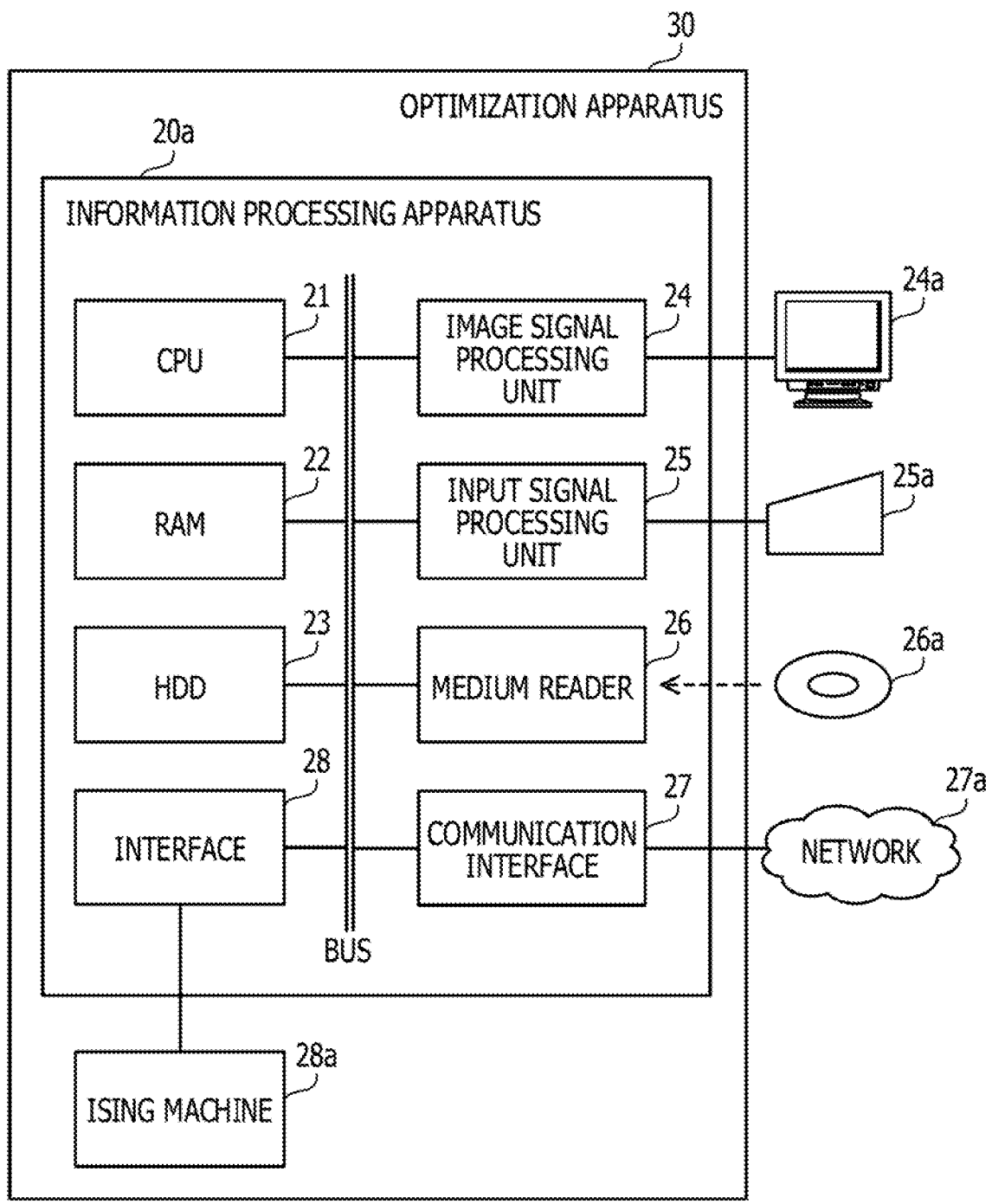
FIG. 4 is a diagram illustrating another hardware example of the optimization apparatus according to the second embodiment.

FIG. 4 is a diagram illustrating another hardware example of the optimization apparatus according to the second embodiment. In FIG. 4, the same elements as those illustrated in FIG. 3 are labeled with the same references.

An optimization apparatus 30 includes an information processing apparatus 20a and an Ising machine 28a. The information processing apparatus 20a has an interface 28. The Interface 28 is coupled to the Ising machine 28a and exchanges data between the CPU 21 and the Ising machine 28a. The interface 28 may be a wired communication interface such as a Peripheral Component Interconnect (PCI) Express or may be a wireless communication interface.

The Ising machine 28a may be hardware that executes simulated annealing or a replica exchange method by using a digital circuit or may be hardware that performs quantum annealing.

Next, functions and processing procedures of the optimization apparatuses 20 and 30 will be described.

Figure 5:
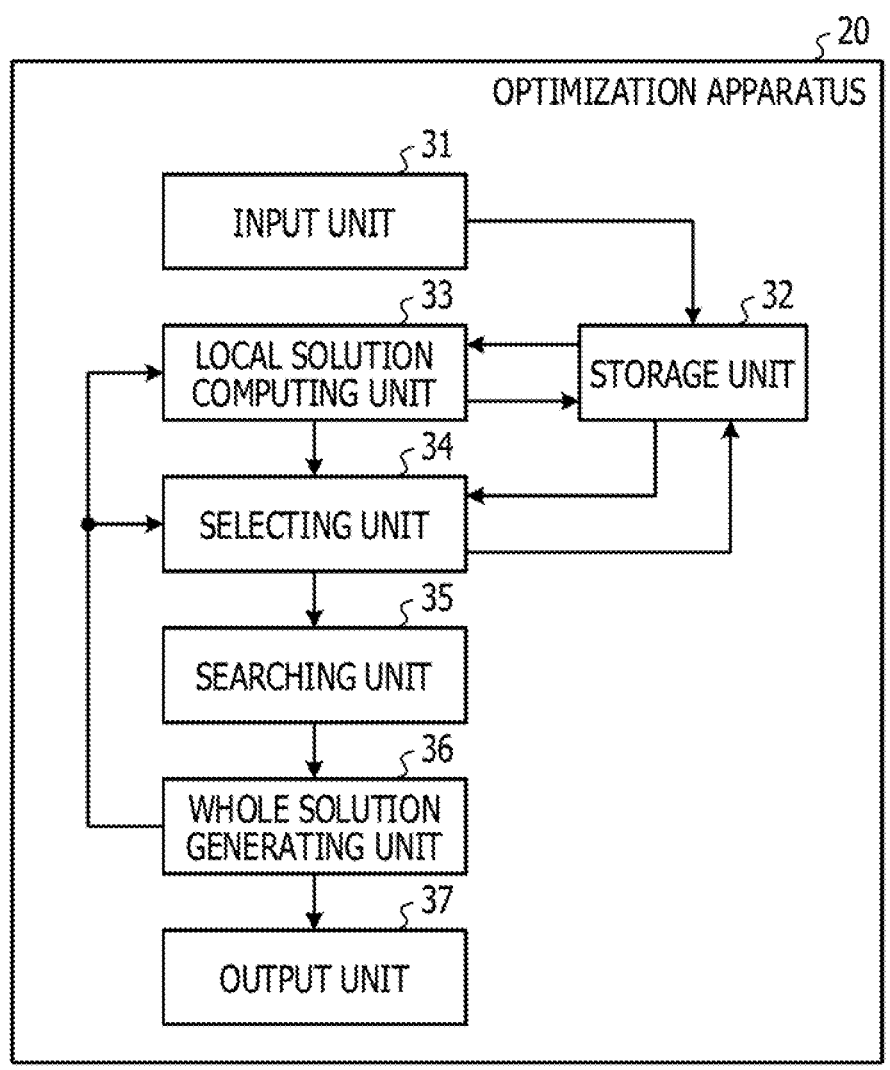
FIG. 5 is a block diagram illustrating a function example of the optimization apparatus according to the second embodiment.

FIG. 5 is a block diagram Illustrating a function example of the optimization apparatus according to the second embodiment.

Although a function example of the optimization apparatus 20 illustrated in FIG. 3 will be described below, the optimization apparatus 30 illustrated in FIG. 4 also have the same functions.

The optimization apparatus 20 includes an input unit 31, a storage unit 32, a local solution computing unit 33, a selecting unit 34, a searching unit 35, a whole solution generating unit 36, and an output unit 37. The input unit 31, the local solution computing unit 33, the selecting unit 34, the searching unit 35, the whole solution generating unit 36 and the output unit 37 may be implemented by program modules executed by the CPU 21, for example. When the optimization apparatus 30 illustrated in FIG. 4 is used, the Ising machine 28a functions as the searching unit 35 (or a part thereof). The storage unit 32 may be implemented by using a storage area secured in the RAM 22 or the HDD 23, for example.

The input unit 31 obtains selection region information input through the input device 25a, for example, and weight coefficients supplied via the network 27a, for example. The optimization apparatus 20 may compute weight coefficients based on input problem data. The selection region information and the weight coefficients are stored in the storage unit 32.

The local solution computing unit 33 computes a local solution of a combinatorial optimization problem by tabu search method, for example, by using the weight coefficients stored in the storage unit 32 based on the evaluation function as expressed in Expression (1). The local solution computing unit 33 may compute a local solution by handling a whole solution generated by the whole solution generating unit 36 as an initial solution.

The selecting unit 34 selects a state variable group targeted by partial problems from a plurality of state variables based on a state variable whose value at a local solution is a predetermined value (assumed as 1 below) among a plurality of state variables, weight coefficients, and input selection region Information. The selecting unit 34 may update the state variable group targeted by the partial problems based on the whole solution generated by the whole solution generating unit 36, instead of the local solutions.

The searching unit 35 searches a ground state for an evaluation function representing partial problems for the state variable group selected by the selecting unit 34. The searching unit 35 may perform the search for a ground state by simulated annealing or Markov chain Monte Carlo methods such as a replica exchange method or may perform the search for a ground state by quantum annealing.

The whole solution generating unit 36 generates a whole solution by updating local solutions based on partial solutions.

The output unit 37 outputs to and causes the display 24a, for example, to display, as a best solution, a whole solution minimizing the value of the evaluation function among whole solutions acquired up to this point. The output unit 37 may store the best solution in the storage unit 32.

Next, an example of the operations of the optimization apparatuses 20 and 30 (control method for the optimization apparatuses 20 and 30) according to the second embodiment will be described.

As an example of a combinatorial optimization problem to be calculated, an amino acid stable structure search that is important in the drug discovery field will be described.

Figure 6:
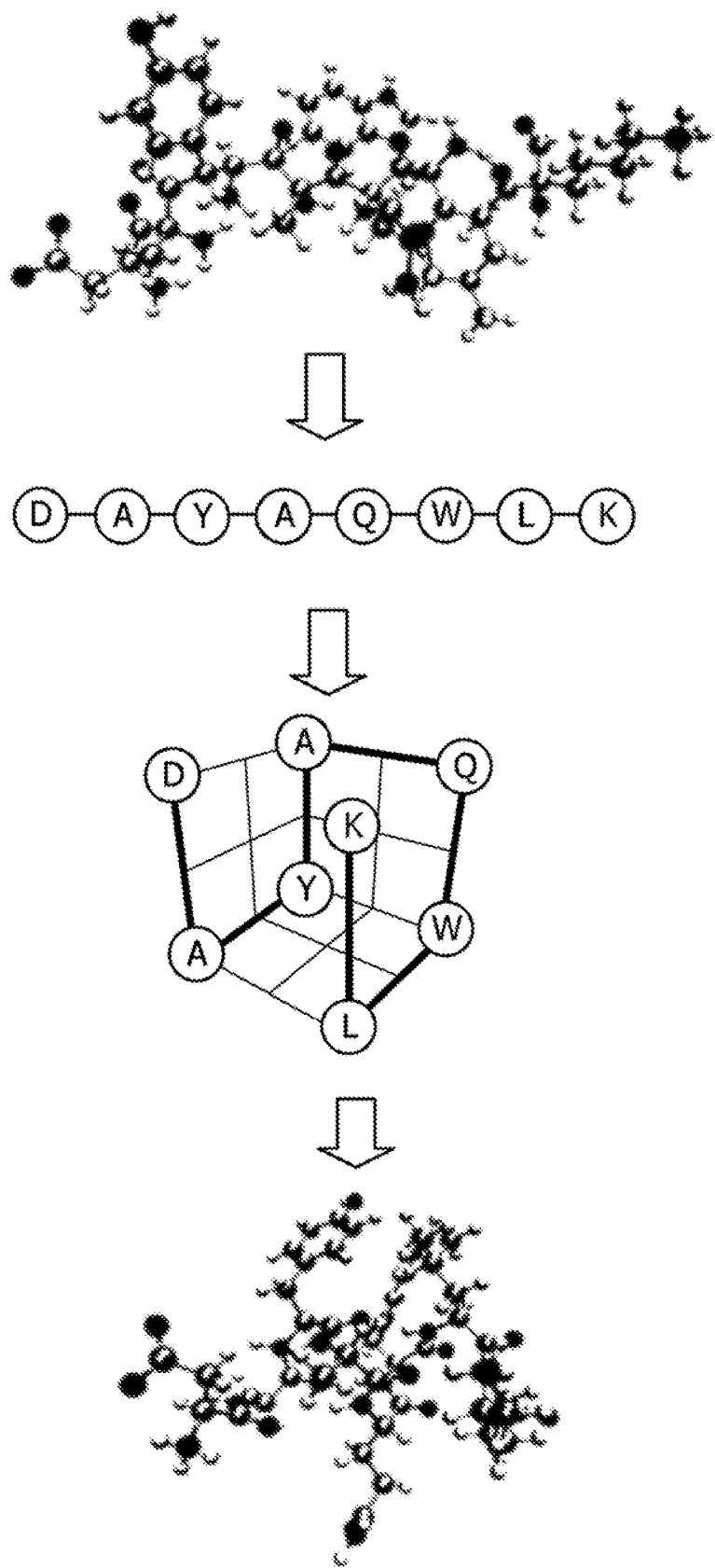
FIG. 6 is a diagram illustrating an example of a process for determining a stable structure of amino acids using a combinatorial optimization method.

FIG. 6 is a diagram illustrating an example of a process for determining a stable structure of amino acids using a combinatorial optimization method.

In a straight-chain structure in which a plurality of amino adds (amino acid residues) as illustrated in FIG. 6 are bonded, it is assumed below that each amino acid is one particle. FIG. 6 illustrates an example in which amino adds in a straight-chain structure with eight amino adds are represented by particles. In the eight particles, "D" indicates an aspartic add, "A" indicates an alanine, "Y" indicates a tyrosine, "Q indicates a glutamine, "W" indicates a tryptophan, "L" Indicates a leucine, and "K" indicates a lycine.

A three-dimensional structure of amino adds is replaced by an Ising model by using a lattice protein (LP) model having amino acids at grid points in a three-dimensional grid space and describing positions of the amino acids in accordance with diamond encoding method.

Referring to FIG. 6, an example of a stable structure acquired by optimization processing using an Ising model is illustrated in a three-dimensional grid space. A solution (stable structure) acquired by optimization processing is used as an initial solution for detail structure calculations such as molecular dynamics calculation. In this manner, by using optimization processing, the total cost for determining a stable structure of amino acids may be reduced.

Although diamond encoding method is described in R. Babbush, and et al., "Construction of Energy Functions for Lattice Heteropolymer Models: A Case Study in Constraint Satisfaction Programming and Adiabatic Quantum Optimization", Advances in Chemical Physics, 155, 201-244, 13 Jun. 2013, it will be described briefly below.

Figure 7:
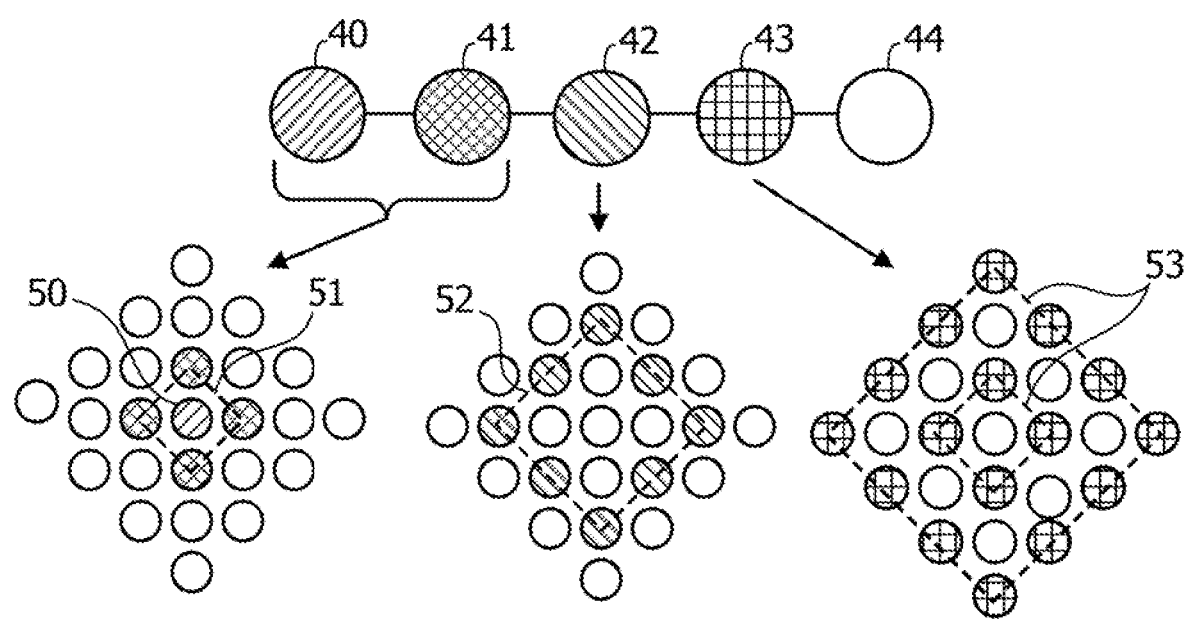
FIG. 7 is a diagram illustrating an example of diamond encoding method.

FIG. 7 is a diagram illustrating an example of diamond encoding method.

In the example in FIG. 7, amino acids 40, 41, 42, 43, and 44 are represented by particles. Diamond encoding method is a method that embeds, in a diamond grid, positions of the amino acids in a straight-chain structure and may express a three-dimensional structure. In FIG. 7, for simplified illustration, an example in which a two-dimensional structure is expressed is illustrated. Each grid point is a candidate where one of a plurality of amino acids is to be placed. The first amino acid 40 in the straight-chain structure is placed at a shell 50 having a grid point at the center of a diamond grid, and the second amino add 41 is placed at one of grid points belonging to a shell 51 adjacent to the shell 50. The third amino acid 42 is placed at one of grid points belonging to a shell 52 adjacent to the shell 51, and the fourth amino acid 43 is placed at one of grid points belonging to a shell 53 adjacent to the shell 52. Also, the fifth amino acid 44 is placed at one of grid points belonging to a shell, not illustrated, adjacent to the shell 53.

There is a constraint that only one amino acid is placed in one shell. In other words, for example, placing two or more amino acids in one shell is inhibited. Some grid points belong to across a plurality of shells. At the grid point, if an amino acid is placed in one shell, no amino acid is placed in the other shell.

Because an LP model is expressed by an Ising model, a state variable included in an evaluation function is allocated to a grid point belonging to each shell.

Figure 8:
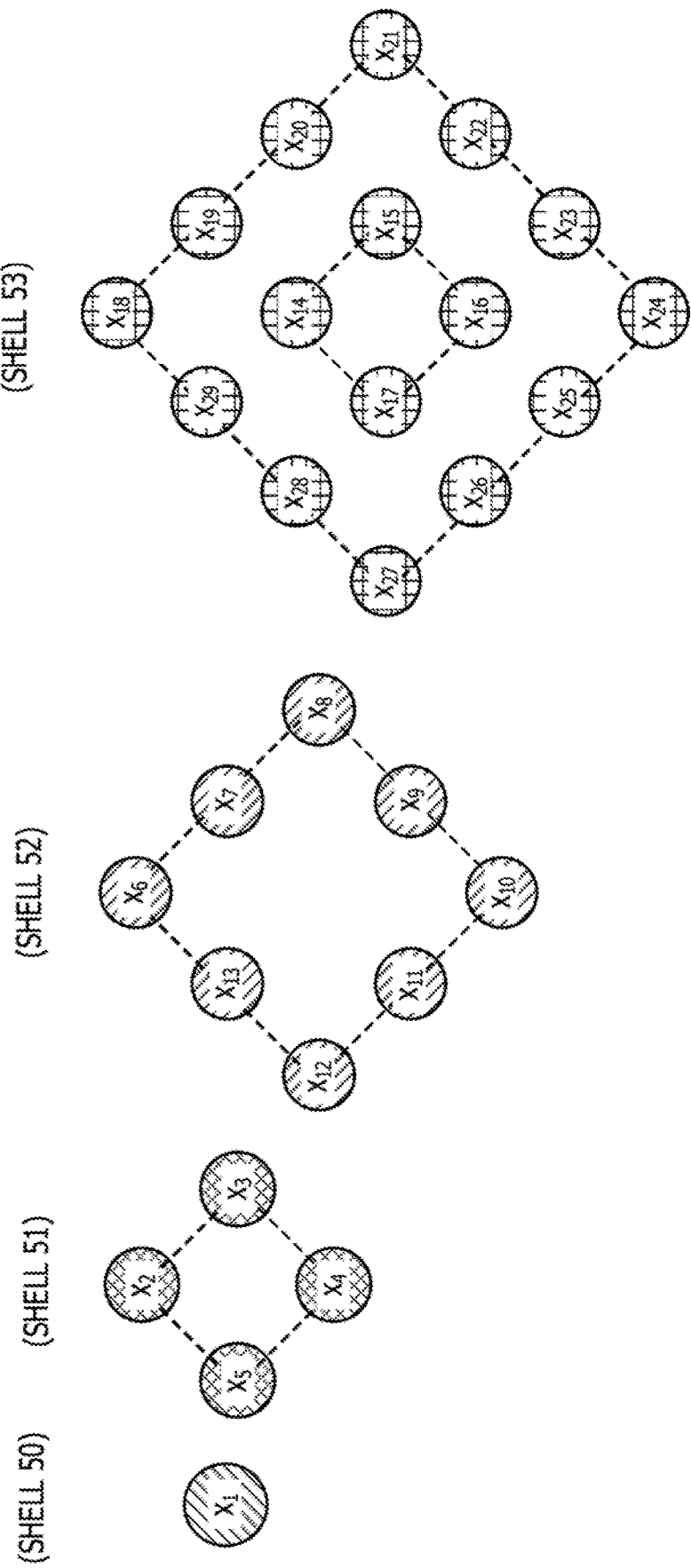
FIG. 8 is a diagram illustrating an example of state variables allocated to grid points of shells.

FIG. 8 is a diagram illustrating an example of state variables allocated to grid points of shells.

$x_1$ is allocated to a grid point belonging to the shell 50, and $x_2$ to $x_5$ are allocated to four grid points belonging to the shell 51. $x_6$ to $x_{13}$ are allocated to eight grid points belonging to the shell 52, and $x_{14}$ to $x_{29}$ are allocated to 16 grid points belonging to the shell 53.

In each of the shells, the values of the state variables allocated to grid points having amino acids are 1.

Figure 9:
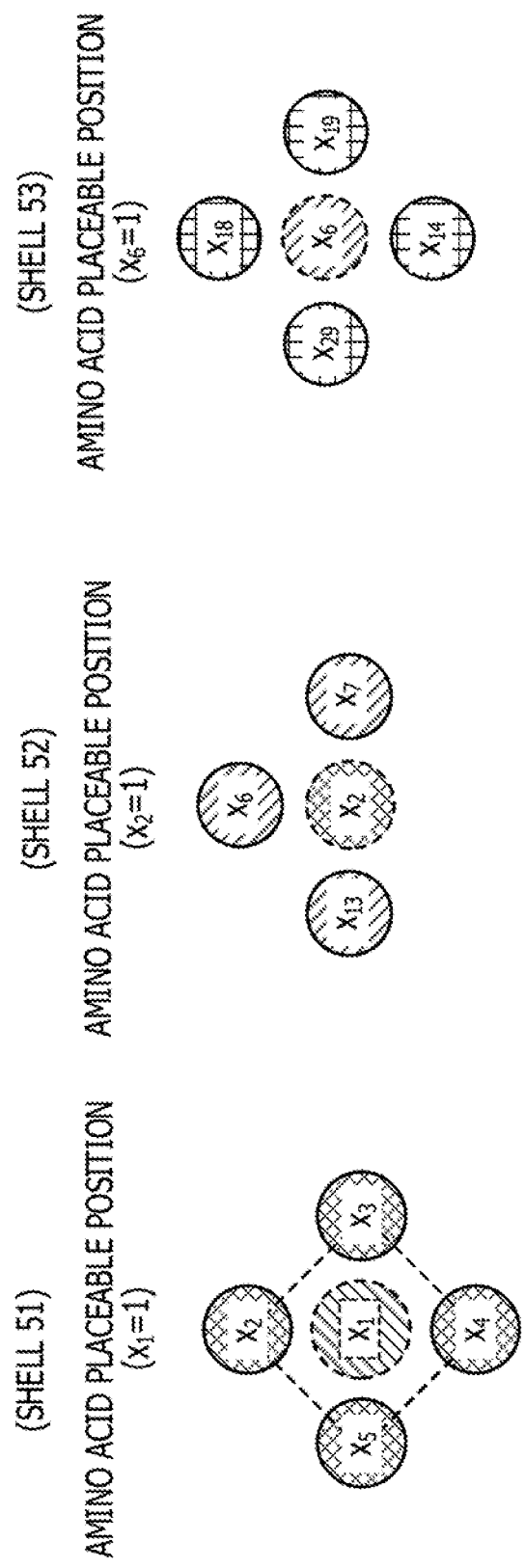
FIG. 9 is a diagram illustrating an example of amino adds placeable positions in shells.

FIG. 9 is a diagram illustrating an example of positions where amino adds may be placed in shells.

When an amino acid is placed at the grid point belonging to the shell 50 ($x_1=1$) and $W_{12}$, $W_{13}$, $W_{14}$, $W_{15} \neq 0$, amino acids are placeable at grid points belonging to the shell 51. When an amino acid is placed ($x_2=1$) at the grid point to which $x_2$ is allocated in the shell 51 and when $W_{26}$, $W_{27}$, $W_{2\,13} \neq 0$, amino acids are placeable at grid points which belong to the shell 52 and to which $x_6$, $x_7$, $x_{13}$ are allocated. When an amino acid is placed at the grid point to which $x_6$ is allocated ($x_6=1$) in the shell 52 and when $W_{6\,14}$, $W_{6\,18}$, $W_{6\,19}$, $W_{6\,29} \neq 0$, amino adds are placeable at grid points which belong to the shell 53 and to which $x_{14}$, $x_{18}$, $x_{19}$, $x_{29}$ are allocated.

The evaluation function of the Ising model acquired by using diamond encoding method may be expressed as $E(x)=H_{one}+H_{conn}+H_{olap}+H_{pair}$.

$H_{one}$ is a constraint term that occurs if a constraint condition that one amino acid exists at one shell is not satisfied and may be expressed by the following Expression (2).

$$H_{one} = \lambda_{one} \sum_{i=0}^{N-1} \sum_{x_a, x_b \in Q_i, a<b} x_a x_b \qquad (2)$$

In Expression (2), N indicates the number of amino adds (corresponding to the number of shells) in a straight-chain structure, and $x_a$ and $x_b$ are state variables allocated to two grid points included in grid point set $Q_j$ belonging to the ith shell. $\lambda_{one}$ is a coefficient having a predetermined magnitude. When $\lambda_{one}$ is set higher, $H_{one}$ becomes higher (stronger constraint) in a case where two or more amino adds exist at one shell.

$H_{conn}$ is a constraint term that occurs if a constraint condition that all amino acids are coupled is not satisfied and may be expressed by the following Expression (3).

$$H_{conn} = \lambda_{conn} \left( N - 1 - \sum_{i=0}^{N-1} \sum_{x_d \in Q_i} \sum_{x_u \in \eta(x_d) \cap Q_{i+1}} x_d x_u \right) \qquad (3)$$

In Expression (3), $x_d$ is a state variable allocated to a grid point included in the grid point set $Q_i$ belonging to the ith shell. $x_{ij}$ is a state variable allocated to a grid point included in a common part of a grid point set $Q_{i+1}$ belonging to the (i+1)th shell and a grid point set $\eta(x_d)$ in which amino adds coupled to the amino acid placed at a grid point to which $x_d$ is allocated may be placed. $\lambda_{conn}$ is a coefficient having a predetermined magnitude. When $\lambda_{conn}$ is set higher, $H_{conn}$ m in a case where the constraint condition that all amino adds are coupled is not satisfied becomes higher (stronger constraint).

$H_{olap}$ is a constraint term that occurs in a case where a constraint condition that a plurality of amino adds is placed at different grid points is not satisfied and may be expressed by the following Expression (4).

$$H_{olap} = \lambda_{olap} \sum_{v \in V} \sum_{x_a, x_b \in \theta(v), a<b} x_a x_b \quad (4)$$

In Expression (4), v is a grid point included in all grid point set V, and $x_a, x_b \in \theta(v)$ represents two state variables $x_a$, $x_b$ allocated to the same grid point v. $\lambda_{olap}$ is a coefficient having a predetermined magnitude. When $\lambda_{olap}$ is set higher, $H_{olap}$ in a case where the constraint condition that a plurality of amino acids is placed at different grid points is not satisfied becomes higher (stronger constraint).

$H_{pair}$ is a cost term to be minimized depending on an interaction between amino acids and may be expressed by the following Expression (5).

$$H_{pair} = \frac{1}{2} \sum_{i=0}^{N-1} \sum_{x_a \in Q_i} \sum_{x_b \in \eta(x_a)} P\omega(x_a)\omega(x_b) x_a x_b \quad (5)$$

In Expression (5), $P\omega(x_a)(x_b)$ represents a magnitude of an interaction caused when $x_a = X_b = 1$. When $P\omega(x_a)(x_b)$ is positive, it means that a repulsive force acts between amino acids placed at two grid points to which $x_a$ and $x_b$ are allocated. When $P\omega(x_a)(x_b)$ is negative, it means that an attractive force acts between amino adds placed at the two grid points to which $x_a$ and $x_b$ are allocated.

$E(x) = H_{one} + H_{conn} + H_{olap} + H_{pair}$ may be varied to an expression using weight coefficients as expressed in Expression (1). The constraint terms as described above are expressed by values of weight coefficients. A weight coefficient having a more significantly high value than those of the other weight coefficients reflects a constraint term.

A guideline for selecting state variables for generating partial problems corresponding to an LP model is as follows.

When partial problems are generated by selecting grid points at which amino acids are placed (or grid points to which state variables having a value of 1 are allocated) simply based on local solutions, there is a possibility that the straight-chain structure itself does not change even by performing a ground state search for the partial problems. Accordingly, a state variable allocated to a grid point that changes the current straight-chain structure by placing an amino acid though no amino acid is currently placed there is to be selected by priority. This is realized by selecting by priority a state variable ($x_j$) with the identification number=j where, when the value of the state variable ($x_i$) allocated to a certain grid point is 1, $W_{ij} \neq 0$.

Figure 10:
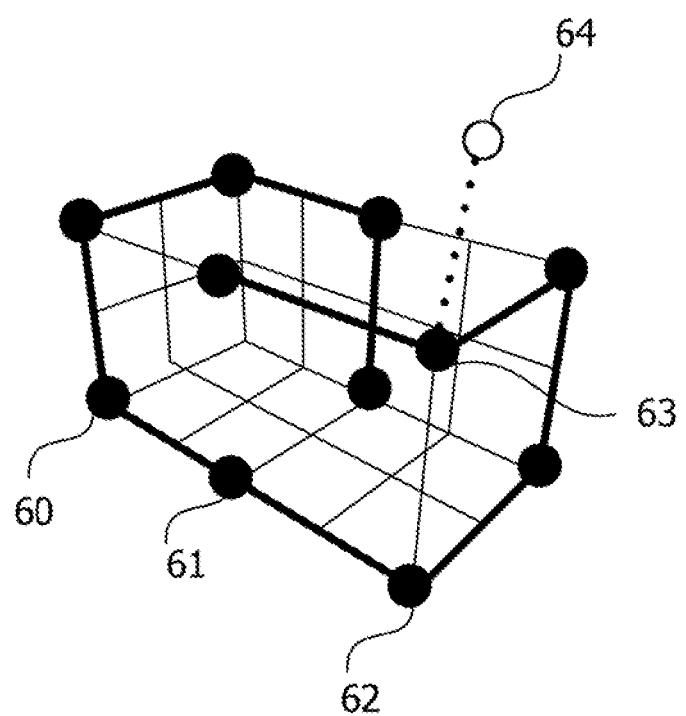
FIG. 10 is a diagram illustrating an example of grid points where amino adds are placed.

FIG. 10 is a diagram illustrating an example of grid points where amino acids are placed.

For example, when state variables allocated to grid points 60, 61, and 62 where amino adds are placed are only selected, there is a possibility that, because of a ground state search, the value of the state variable allocated to one of the grid points 60 to 62 changes to 0 (meaning that no amino acid is placed there). However, the three-dimensional structure itself does not change.

On the other hand, when there is an Interaction between state variables allocated to a grid point 63 where an amino acid is placed and a grid point 64 where no amino acid is placed (with a weight coefficient of non-zero), there is a possibility that the three-dimensional structure changes because of a search if the state variable allocated to the grid point 64 is selected.

The selecting unit 34 illustrated in FIG. 5 selects a state variable group targeted by partial problems from a plurality of state variables as described above based on a state variable whose value in local solutions is 1 among a plurality of state variables and the weight coefficients. The selecting unit 34 limits the number of variables to be included in the state variable group based on the selection region Information. This point will be described below.

An example of a control method for the optimization apparatuses 20 and 30 according to the second embodiment will be described below. The whole processing flow is the same as the processing flow illustrated in FIG. 2. An example of the processing for selecting a state variable group (processing for generating partial problems) (corresponding to the processing in step S3 in FIG. 2) by the optimization apparatuses 20 and 30 according to the second embodiment will be described below.

Figure 11:
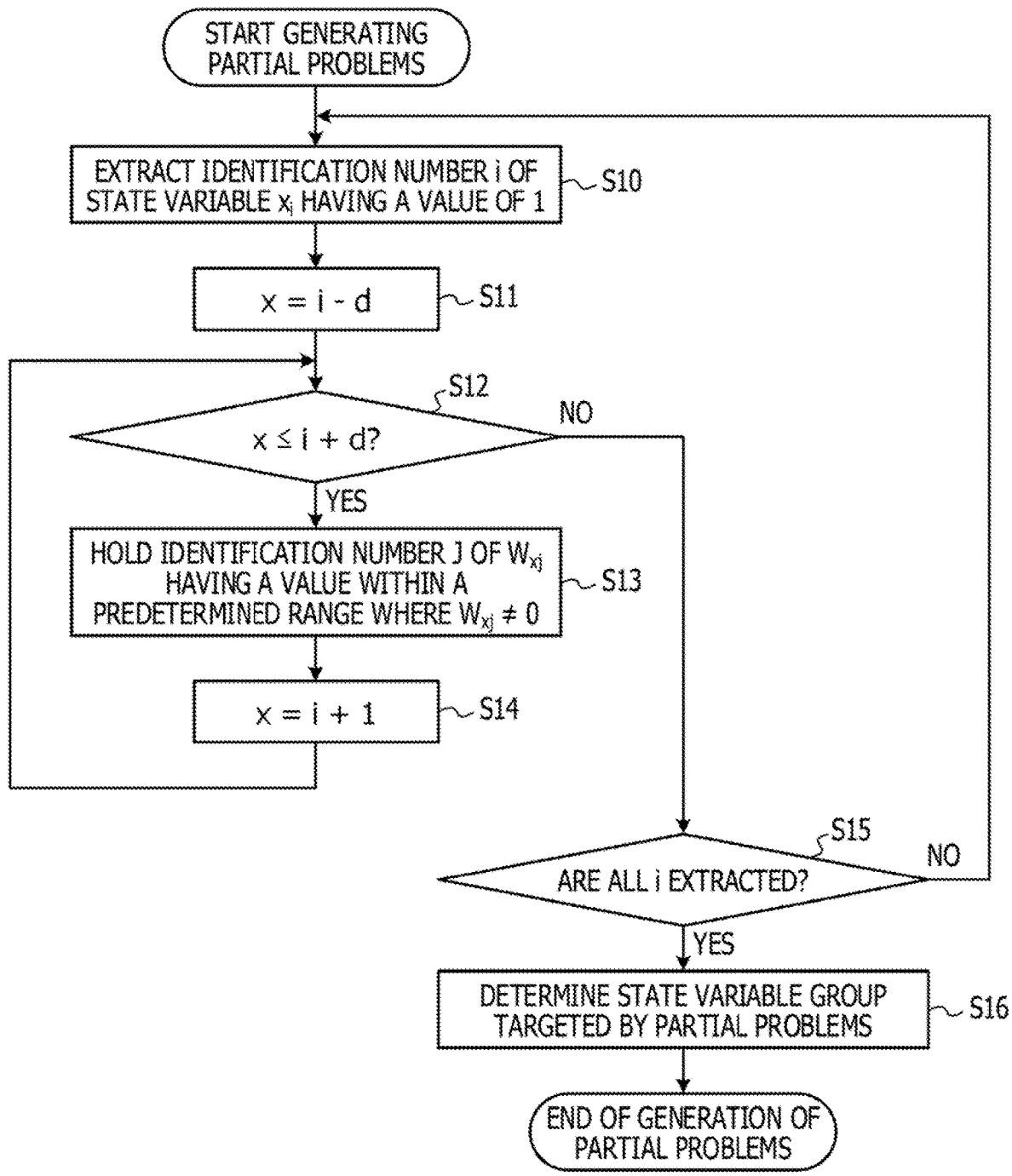
FIG. 11 is a flowchart illustrating a flow of an example of processing for generating partial problems.

FIG. 11 is a flowchart illustrating a flow of an example of processing for generating partial problems.

The selecting unit 34 extracts one identification number i of a state variable x having a value of 1 from local solutions (or a whole solution) (step S10) and sets a certain variable x as x=i−d (step S11). d is a value included in the selection region information and is a value to be set for increasing the number of state variables to be included in a state variable group. d is determined in accordance with the number of computing bits processable by the searching unit 35, for example.

After the processing in step S11, the selecting unit 34 determines whether x≤i+d is satisfied or not (step S12). If it is determined that x≤i+d is satisfied, the selecting unit 34 causes the storage unit 32 to hold the Identification number j of $W_{xj}$ having a value within a predetermined range where $W_{xj} \neq 0$ (step S13). The predetermined range is determined such that, for example, a state variable allocated to a grid point influenced by an interaction between amino acids when the amino acids are placed at grid points is only selected.

For example, the predetermined range is determined such that one of the following conditions is satisfied by using arbitrary parameters A to D that are externally settable.

| | |
|---|---|
| A≤$W_{xj}$≤B and $W_{xj} \neq 0$ and A=B | Condition 1 |
| A≤$W_{xj}$≤B and $W_{xj}$≤B and A≠B | Condition 2 |
| (A≤$W_{xj}$≤B or C≤$W_{xj}$≤D) and $W_{xj} \neq 0$ and A≠B≠C≠D | Condition 3 |
| (A≤$W_{xj}$ or $W_{xj}$≤B) and $W_{xj} \neq 0$ and B≤A | Condition 4 |

For example, when the maximum value of $|W_{xj}|$ determined by an interaction between amino adds is $J_0$, $-J_0 \leq W_{xj} \leq J_0$ is set (corresponding to the case where A=$-J_0$, B=$J_0$ in Condition 2 above). Different predetermined ranges may be set for each weight coefficient. Information on the predetermined range is included in the selection region information.

After the processing in step S13, the selecting unit 34 defines asx=x+1 (step S14) and repeats the processing from step S12.

Figure 12:
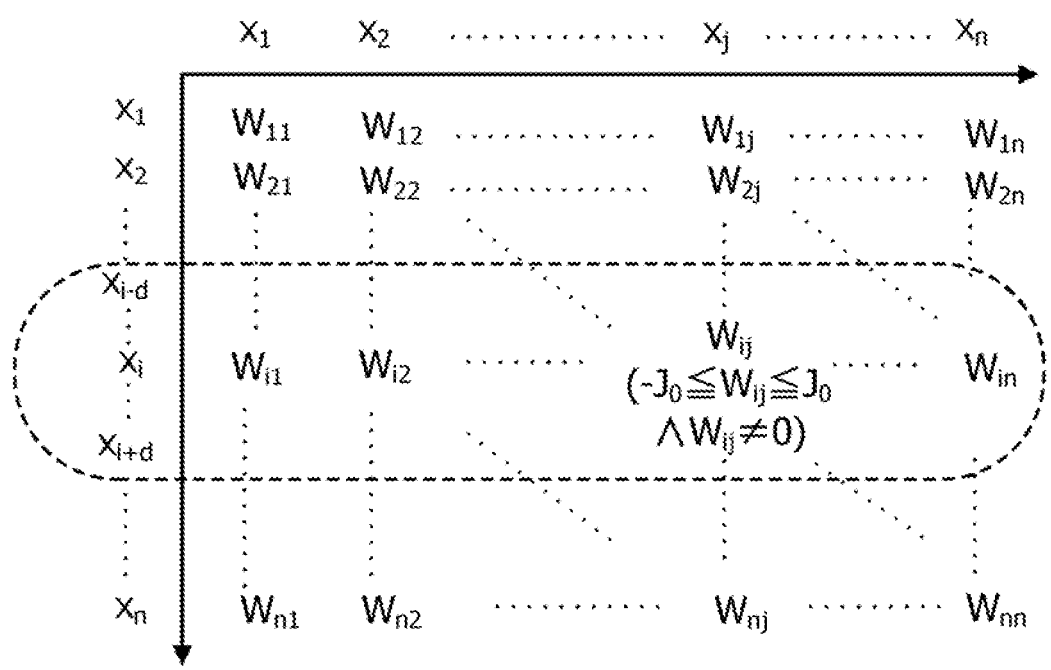
FIG. 12 is a diagram illustrating an example of held identification numbers j.

FIG. 12 is a diagram illustrating an example of identification numbers j to be held.

In a coefficient matrix with weight coefficients as illustrated in FIG. 12, when $x_i=1$, an identification number (j in the example in FIG. 12) other than i of two identification numbers of weight coefficients having values that are not 0 and are not equal to or higher than $-J_0$ and not equal to or lower than $J_0$ among $W_{i1}$ to $W_{in}$ is held. The same processing is performed on $x_{i-d}$ to $x_{i+d}$ irrespective of whether the value is 0 or 1.

If it is determined in the processing in step S12 that x≤i+d is not satisfied, the selecting unit 34 determines whether all of identification numbers i of the state variables x having a value of 1 have been extracted or not (step S15). If it is determined that all of the identification numbers i have not been extracted, the selecting unit 34 repeats the processing from step S10.

If it is determined that all of the identification numbers i of the state variables $x_i$ having a value of 1 have been extracted, the selecting unit 34 determines a state variable group targeted by the partial problems based on the held identification numbers j (step S16) and ends the generation of the partial problems.

For example, the selecting unit 34 selects all of state variables with the held identification numbers j and includes them in the state variable group. The selecting unit 34 adds state variables with identification numbers that are not held in decreasing order (or increasing order) of identification numbers to the state variable group up to the number of computing bits processable by the searching unit 35. The selecting unit 34 may randomly add state variables with identification numbers that are not held to the state variable group based on random numbers up to the number of computing bits processable by the searching unit 35.

In a case where the number of computing bits processable by the searching unit 35 is low, for example, the selecting unit 34 may not include state variables with identification numbers that are not held in the state variable group targeted by the partial problems. In this case, the selecting unit 34 may select state variables with identification numbers among state variables with the held identification numbers j in decreasing or increasing order of the identification numbers or randomly up to the number of computing bits processable by the searching unit 35 and include them in the state variable group.

The selecting unit 34 may determine state variables to be included in the state variable group based on a comparison result between the number of computing bits processable by the searching unit 35 and the number of the held Identification numbers j.

Figure 13:
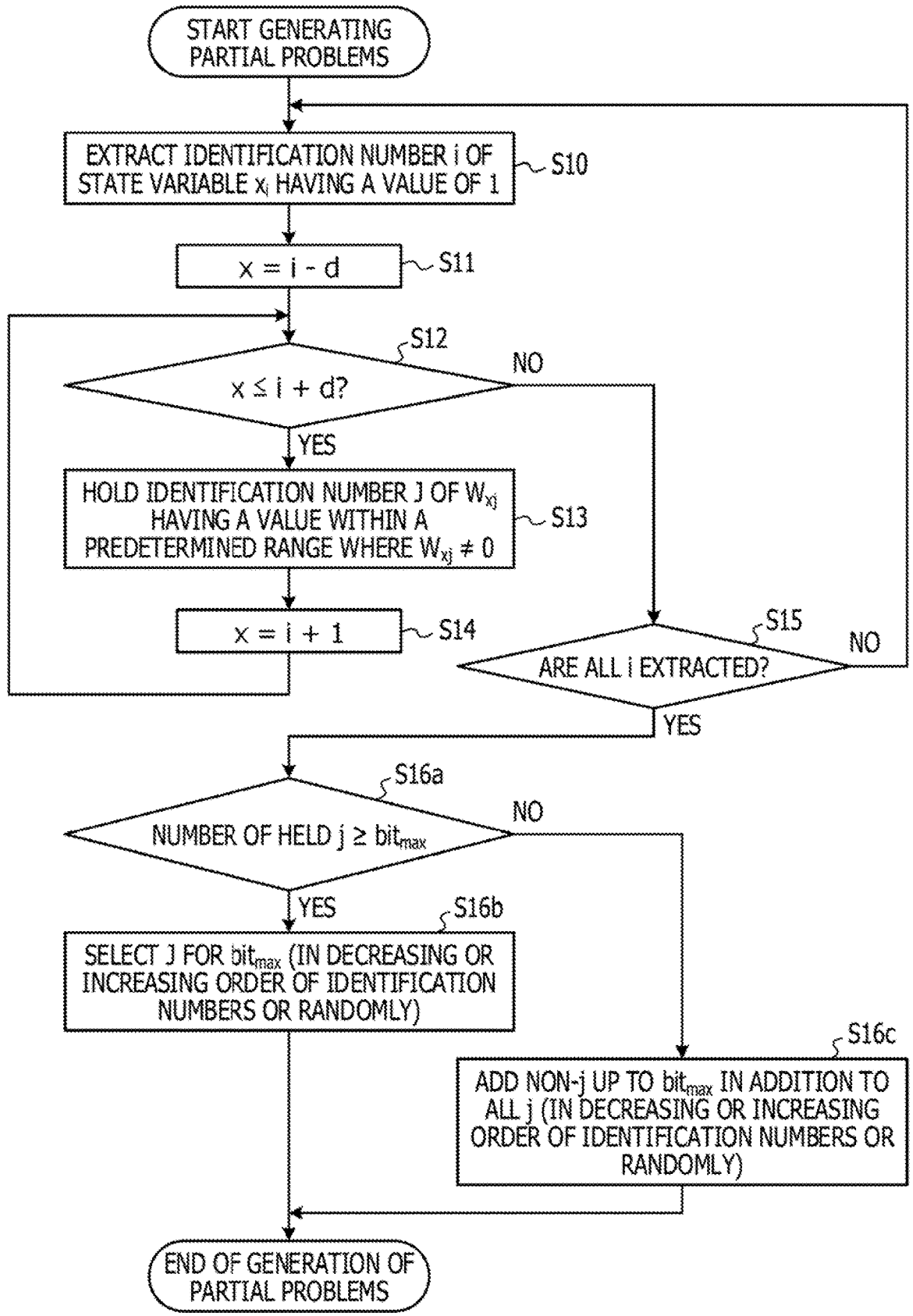
FIG. 13 is a flowchart illustrating a flow of another example of the processing for generating partial problems.

FIG. 13 is a flowchart illustrating a flow of another example of the processing for generating partial problems.

The processing up to step S15 is the same as the processing illustrated in FIG. 11. After the processing in step S15, the selecting unit 34 determines whether the number of the held identification numbers j is equal to or higher than the number ($bit_{max}$) of computing bits processable by the searching unit 35 or not (step S16a). If it is determined that the number of the identification numbers j is equal to or higher than $bit_{max}$, the selecting unit 34 selects state variables with the identification numbers j for $blt_{max}$ in decreasing or increasing order of Identification numbers or randomly and Includes them in the state variable group (step S16b) and ends the generation of the partial problems. If it is determined that the number of the identification numbers j is not equal to or higher than $bit_{max}$, the selecting unit 34 adds state variables with identification numbers (non-j) that are not held to the state variable group up to the number corresponding to $bit_{max}$ in addition to all of state variables with the identification numbers j. As a method for adding non-j state variables to the state variable group, there is a method that adds state variables in decreasing or increasing order of identification numbers or randomly as described above. After the processing in step S16c, the selecting unit 34 ends the generation of the partial problems.

Calculation Example 1

A result of calculation of a stable structure determination problem for a straight-chain structure with 20 amino acids (amino acid residues=20) for which a value (lowest energy) of an evaluation function with a ground state (optimum solution) is known will be described below. The size of the problem (or bit size of the problem) is 7.8 kbits. The lowest energy is −5823.

The used hardware is the optimization apparatus 30 (FIG. 4) including the Ising machine 28a (1 kbit size) that performs a ground state search by simulated annealing by using a digital circuit.

The number of iterations of the main loop illustrated in FIG. 2 was three, the number of Iterations of the subloop was two, and the number of iterations of the state updating processing by the Ising machine 28a for one subloop was $10^6$, and d above included in the selection region information was 1. The range of values of the weight coefficients to be used for selecting a state variable group targeted by partial problems satisfies one of Conditions 1 to 4 as described above, for example, and the state variable group targeted by partial problems was equal to or lower than 1 kbits.

Percentages of correct answers were evaluated for 100 trials with different seed values for random numbers to be used for selecting a state variable group targeted by partial problems.

When al state variables targeted by partial problems were selected randomly based on random numbers for comparison, the solutions fell into local solutions, and the lowest evaluation function values acquired from 100 trials was −5624. In other words, for example, the percentage of correct answers was 0. The calculation time was 26.4 seconds per trial.

On the other hand, when the selecting unit 34 generates partial problems through the processing as described above, the evaluation function values were −5823 at 86 trials of 100 trials, and an optimum solution was acquired. In other words, for example, the percentage of correct answers was 0.86. The calculation time was 26.5 seconds per trial.

Calculation Example 2

Next, a result of calculation of a stable structure determination problem for a straight-chain structure with 48 amino acids (amino acid residues=48) for which lowest energy is known will be described. The size of the problem (or bit size of the problem) is 31 kbits. The lowest energy is −2615.

The used hardware is the optimization apparatus 30 (FIG. 4) including the Ising machine 28a (8 kbit size) that performs a ground state search by simulated annealing by using a digital circuit.

The number of iterations of the main loop illustrated in FIG. 2 was three, the number of Iterations of the subloop was two, and the number of Iterations of the state updating processing by the Ising machine 28a for one subloop was $2 \times 10^7$, and d above included in the selection region information was 1. The range of values of the weight coefficients to be used for selecting a state variable group targeted by partial problems satisfied one of Conditions 1 to 4 as described above, for example, and the state variable group targeted by partial problems was equal to or lower than 8 kbits.

Percentages of correct answers were evaluated for 100 trials with different seed values for random numbers to be used for selecting a state variable group targeted by partial problems.

When the selecting unit 34 generated partial problems, the evaluation function values were −2615 at 99 trials of 100 trials, and an optimum solution was acquired. In other words, for example, the percentage of correct answers was 0.99. The calculation time was 56.4 seconds per trial.

FIG. 14 is a diagram illustrating a comparison example of amounts of complexity based on the presence of division of a problem.

FIG. 14 illustrates comparison results of the amounts of complexity for two problems in a case where a problem is solved by generating partial problems by the optimization apparatus 30 and a case where the problem is solved directly by a simulator without dividing the problem. "DIVIDED (HARDWARE)" indicates the case where a problem is solved by generating partial problems by the optimization apparatus 30, and "NON-DIVIDED (SIMULATION)" Indicates the case where the problem is solved directly by a simulator without dividing the problem.

The PROBLEM BIT SIZE indicates sizes of the two problems described above. The OPTIMIZATION CALCULATION BIT SIZE indicates the number of computing bits processable by the Ising machine 28a when the optimization apparatus 30 solves the problem by generating partial problems and is equal to the problem bit size when the problem is solved directly by a simulator without dividing the problem.

The NUMBER OF HARDWARE CALLS is the number of times of use of the Ising machine 28a (the number of times of performing the processing in step S4) when the optimization apparatus 30 solves the problem by generating partial problems. When the problem bit size is 3.10E+04(31 k) bits, the number of hardware calls is 5. When the problem bit size is 7.80E+03(7.8 k) bits, the number of hardware calls is 6. The number of hardware calls when a simulator solves the problem is 1. The number of iterations of search processing by the Ising machine 28a per one hardware call is 2.00E+07 when the problem bit size is 3.10E+04 bits and is 1.00E+06 when the problem bit size is 7.80E+03 bits. The number of iterations in a case where a simulator solves the problems is 7.42E+06 when the problem bit size is 3.10E+04 bits and is 2.33E+06 when the problem bit size is 7.80E+03 bits.

The PERCENTAGE OF CORRECT ANSWERS is 0.99 in the problem with a problem bit size of 3.10E+04 bits and is 0.86 in the problem with a problem bit size of 7.80E+03 in a case where the optimization apparatus 30 solves the problems by generating partial problems. Both of the percentages of correct answers when a simulator solves the problems are 0.99 where the problems has two sizes.

The TOTAL NUMBER OF ITERATIONS is 1.00E+08 in the problem with a problem bit size of 3.10E+04 bits and is 6.00E+06 in the problem with a problem bit size of 7.80E+03 when the optimization apparatus 30 solves the problems by generating partial problems. The total number of iterations when a simulator solves the problems is 7.42E+06 in the problem with a problem bit size of 3.10E+04 bits and is 2.33E+06 in the problem with a problem bit size of 7.80E+03.

The iteration to solution (ITS) (the number of iterations for acquiring a correct answer with a probability of 99%) is equal to the total number of iterations except for the case where the optimization apparatus 30 generates partial problems to solve the problem with a problem bit size of 7.80E+03. It was found that when the amount of complexity (calculation cost) is expressed by ITS x OPTIMIZATION CALCULATION BIT SIZE, an increase of the amount of complexity is 8.00E+11/2.30E+11 or approximately 3.5 times compared with the case where the problem with a large size was solved without dividing it. On the other hand, compared with the case where the problem with a small size is solved without dividing it, the amount of complexity is 1.41E+10/1.82E+10 or approximately 0.77 times, and it was found that the amount of complexity is lower than that of the calculation without dividing the problem.

Having described above a problem for determining a stable structure of a straight-chain structure with a plurality of amino acids as an example of a combinatorial optimization problem to be calculated, other combinatorial optimization problems such as a traveling salesman problem may also be solved by generating partial problems. In order to solve a traveling salesman problem, each state variable indicates whether a salesman is present in a certain city at a certain time or not instead of indication of whether an amino acid is placed at a grid point or not. If a salesman is present in a certain city at a certain time, the value of the state variable corresponding to the time and the city is 1, for example. The partial problems may be generated by the same processing as the processing illustrated in FIG. 11 or FIG. 13.

Third Embodiment

A method for selecting state variables for generating partial problems in consideration of a shell structure as illustrated in FIGS. 7 to 9 will be described below.

The selecting unit 34 may select a state variable group from state variables allocated to grid points belonging to one shell. In this case, the selecting unit 34 selects $x_j$ corresponding to the identification number j of $W_{ij}$ having a value within a predetermined range where $W_{ij} \neq 0$ from the other state variables in the shell to which x having a value of 1 belongs.

However, when the identification number i is dose to the maximum value or minimum value of the identification numbers of the state variables within the same shell and when the state variables to be selected are determined in a range of i±d, a state variable in another shell is selected. There is a possibility that a constraint condition violation occurs.

For example, assuming d=2 when $x_6$=1 in the shell 52 as illustrated in FIG. 8, i−d=6−2=4. There is a possibility that $x_4$ being a state variable in the shell 51 has 1 instead of $x_6$. Accordingly, the selecting unit 34 generates partial problems by selecting state variables through the following processing, for example.

Figure 15:
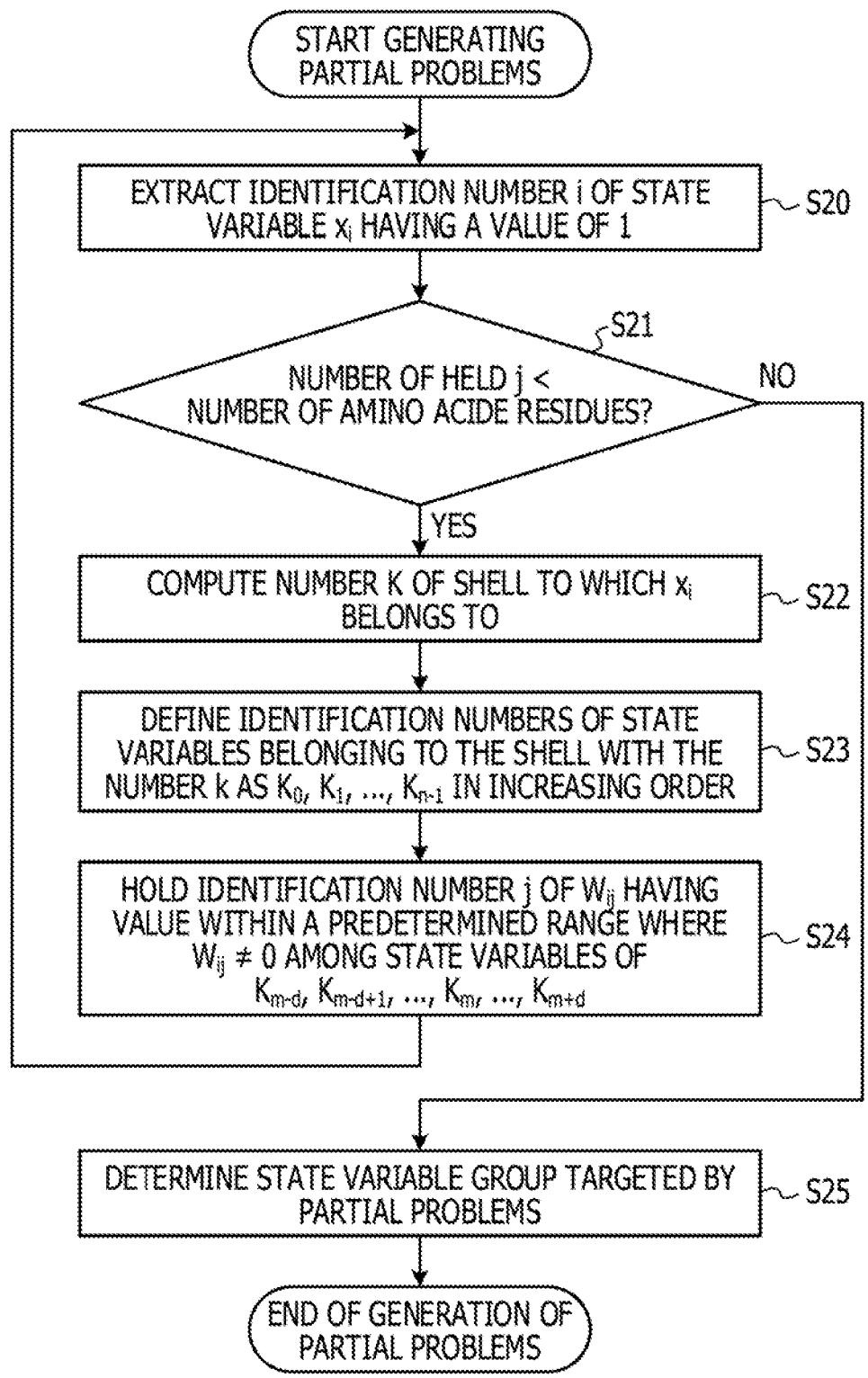
FIG. 15 is a flowchart illustrating a flow of an example of processing for generating partial problems according to a third embodiment.

FIG. 15 is a flowchart illustrating a flow of an example of processing for generating partial problems according to a third embodiment.

First, the selecting unit 34 extracts one identification number i of state variables x having a value of 1 from local solutions (or whole solution) (step S20). The selecting unit 34 determines whether the number of held identification numbers j is lower than the number of amino acids (the number of amino acid residues) included in a straight-chain structure or not (step S21).

If it is determined that the number of identification numbers j is lower than the number of amino acid residues, the selecting unit 34 computes a number k of the shell to which x belongs (step S22). The selecting unit 34 defines the identification numbers of state variables belonging to the shell with the number k as $K_0, K_1, \ldots, K_{n-1}$ in increasing order (step S23). n is the number of state variables belonging to the shell with the number k.

For example, in the example of the shell 52 illustrated in FIG. 8, n=8, and $K_0$=6, $K_1$=7, $K_2$=8, $K_3$=9, $K_4$=10, $K_5$=11, $K_6$=12, and $K_7$=13.

Assuming that i=$K_m$ and a variable for determining a selection range for state variables is d (included in the selection region information), the selecting unit 34 holds the identification numbers j of $W_{ij}$ having values within a predetermined range where $W_{ij} \neq 0$ among state variables of $K_{m-d}, K_{m-d+1}, \ldots, K_m, \ldots, K_{m+d}$ (step S24). The selecting unit 34 assumes that $K_0$ to $K_{n-1}$ are coupled in circular permutation and handles state variables of $K_{m-d}$ to $K_{m+d}$ as selection candidates from state variables of $K_0$ to $K_{n-1}$. For example, when $K_m$=$K_{n-1}$, $K_{m+d}$ is $K_{0+d-1}$ (when d=2, $K_{m+2}$=$K_1$). When $K_m$=$K_0$, $K_{m-d}$ is $K_{n-1-d+1}$ (when n=8 and d=2, $K_{m-2}$=$K_6$).

Figure 16:
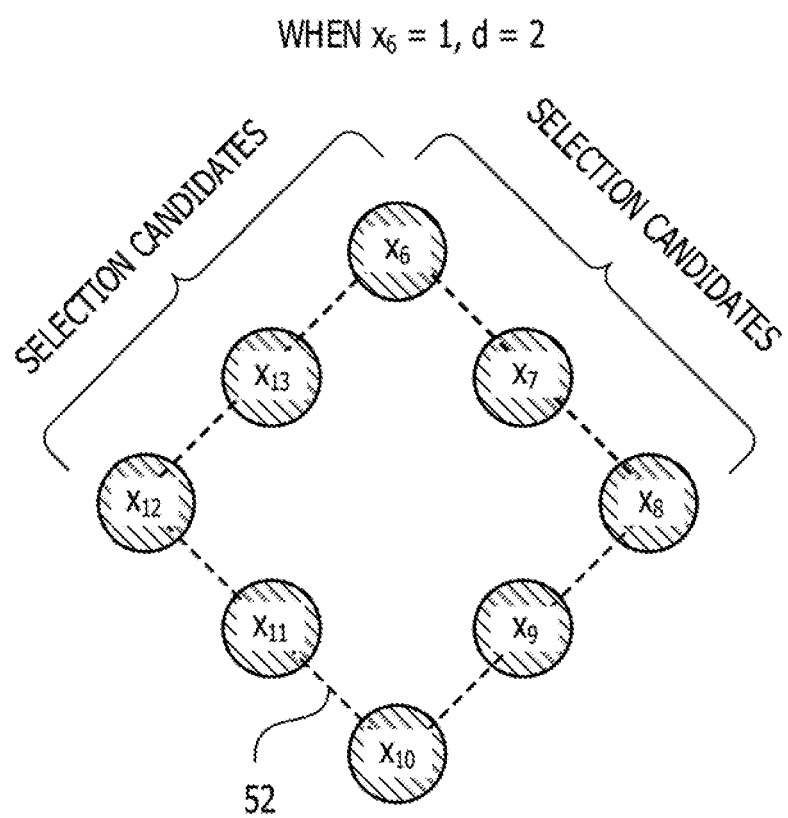
FIG. 16 is a diagram illustrating an example of state variables being selection candidates in a certain shell.

FIG. 16 is a diagram illustrating an example of state variables being selection candidates in a certain shell.

FIG. 16 illustrates examples of state variables being selection candidates when $x_6$=1, d=2 in the shell 52. When $x_6$=1 or i=$K_m$=6, $K_{m-d}$ to $K_{m+d}$ above are $K_6$ (=12), $K_7$ (=13), $K_0$ (=6), $K_1$ (=7), $K_2$ (=8). In other words, for example, $x_{12}, x_{13}, x_6, x_7, x_8$ are state variables being selection candidates, and the identification number j of $W_{6j}$ having a value within a predetermined range where $W_{6j} \neq 0$ is held among the identification numbers (12, 13, 6, 7, 8).

After the processing in step S24, the processing from step S20 is repeated. If it is determined in the processing in step S21 that the number of held identification numbers j is not lower than the number of amino acid residues, the selecting unit 34 determines a state variable group targeted by partial problems based on the held identification numbers j (step S25) and ends the generation of the partial problems. In the processing in step S25, various determination methods are applicable, like the processing in step S16 above. Instead of the processing in step S25, the processing in steps S16a to S16c illustrated in FIG. 13 is also applicable.

By using the method for generating partial problems as described above, partial problems may be generated that are proper for a problem for determining a stable structure of amino acids using an LP model and diamond encoding method. Thus, further suppression of the amount of complexity may be expected.

As described above, the above processing details may be realized by causing the optimization apparatus 20 or 30 to execute a program.

The program may be recorded on a computer-readable recording medium (such as the recording medium 26a). As the recording medium, such as a magnetic disk, an optical disk, a magneto-optical disk, and a semiconductor memory may be used. The magnetic disk includes an FD and an HDD. The optical disk includes a CD, a CD-recordable (R)/rewritable (RW), a DVD, and a DVD-R/RW. The program may be recorded and distributed on a portable recording medium. In that case, the program may be copied from the portable recording medium to another recording medium (such as the HDD 23) and executed.

As described above, although one aspect of an optimization apparatus, a control method for the optimization apparatus and a control program for the optimization apparatus according to the present disclosure has been described based on the embodiments, such an aspect is a mere example and is not limited to the above description.

For example, having described that, in the example above, d that is a value to be set for increasing the number of state variables to be included in a state variable group is a fixed value, the number of state variables to be included in a state variable group may be increased to the number of computing bits processable by the searching unit 35.

All examples and conditional language provided herein are intended for the pedagogical purposes of aiding the reader in understanding the invention and the concepts contributed by the Inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An optimization apparatus comprising:
  a memory; and
  a processor coupled to the memory and the processor configured to:
    compute a local solution for a combinatorial optimization problem based on a first evaluation function representing the combinatorial optimization problem,
    select a state variable group targeted by partial problems from the plurality of state variables based on a first state variable whose value at the local solution is a predetermined value among the plurality of state variables included in the first evaluation function, a weight coefficient representing a magnitude of an interaction between the plurality of state variables held in a storage unit, and input selection region information,
    search a ground state for a second evaluation function representing the partial problems for the selected state variable group, and
    generate a whole solution by updating the local solution based on the partial solutions acquired by the ground state search.

2. The optimization apparatus according to claim 1, wherein the processor is further configured to select a second state variable that interacts with the first state variable based on the weight coefficient as a candidate to be included in the state variable group.

3. The optimization apparatus according to claim 1, wherein the processor is further configured to update the state variable group to be selected based on a third variable state whose values in the generated whole solution is the predetermined value, the weight coefficient, and the selection region information.

4. The optimization apparatus according to claim 1, wherein the processor is further configured to compute the local solution by handling the generated whole solution as an initial solution.

5. The optimization apparatus according to claim 1, wherein
the selection region information includes information on the number of computing bits, and
the processor is further configured to select the state variable group with an equal number of state variables to the number of computing bits.

6. The optimization apparatus according to claim 2, wherein
the combinatorial optimization problem is a problem for searching a stable structure of a straight-chain structure with a plurality of amino acids, and each of the plurality of state variables is allocated to one of a plurality of grid points that are candidates at which one of the plurality of amino acids is to be placed, and
the processor is further configured to select the second state variable that interacts with the first state variable allocated to a grid point at which an amino acid is placed as a candidate to be included in the state variable group.

7. The optimization apparatus according to claim 6, wherein the processor is further configured to select the state variable group from state variables allocated to grid points belonging to an identical shell where placing two or more amino acids is inhibited.

8. A control method executed by a processor included in an optimization apparatus, the control method comprising:
computing a local solution for a combinatorial optimization problem based on a first evaluation function representing the combinatorial optimization problem;
selecting a state variable group targeted by partial problems from the plurality of state variables based on a first state variable whose value at the local solution is a predetermined value among the plurality of state variables included in the first evaluation function, a weight coefficient representing a magnitude of an interaction between the plurality of state variables held in a storage unit, and input selection region information;
searching a ground state for a second evaluation function representing the partial problems with respect to the selected state variable group; and
generating a whole solution by updating the local solution based on the partial solutions acquired by the ground state search.

9. A non-transitory computer-readable recording medium having stored therein a control program for an optimization apparatus for causing a computer to execute a process comprising:
computing a local solution for a combinatorial optimization problem based on a first evaluation function representing the combinatorial optimization problem;
selecting a state variable group targeted by partial problems from the plurality of state variables based on a first state variable whose value at the local solution is a predetermined value among the plurality of state variables included in the first evaluation function, a weight coefficient representing a magnitude of an interaction between the plurality of state variables held in a storage unit, and input selection region information;
searching a ground state for a second evaluation function representing the partial problems for the selected state variable group; and
generating a whole solution by updating the local solution based on the partial solutions acquired by the ground state search.

* * * * *